United States Patent
Duong et al.

(10) Patent No.: US 7,361,187 B2
(45) Date of Patent: Apr. 22, 2008

(54) THREADED CRYOSTAT FOR CRYOSURGICAL PROBE SYSTEM

(75) Inventors: Thach Duong, Tustin, CA (US); James Q. Dinh, Tustin, CA (US)

(73) Assignee: Endocare, Inc., Irvine, CA (US)

( * ) Notice: Subject to any disclaimer, the term of this patent is extended or adjusted under 35 U.S.C. 154(b) by 540 days.

(21) Appl. No.: 10/954,433

(22) Filed: Sep. 30, 2004

(65) Prior Publication Data

US 2005/0043725 A1 Feb. 24, 2005

Related U.S. Application Data

(63) Continuation-in-part of application No. 10/828,031, filed on Apr. 20, 2004, now Pat. No. 7,160,291, which is a continuation-in-part of application No. 10/603,883, filed on Jun. 25, 2003, now Pat. No. 7,207,985.

(51) Int. Cl.
*A61F 7/00* (2006.01)

(52) U.S. Cl. .................. 607/105; 607/107; 606/20; 606/23

(58) Field of Classification Search ............... 607/105, 607/107; 606/20–23; 62/293
See application file for complete search history.

(56) References Cited

U.S. PATENT DOCUMENTS

| | | | |
|---|---|---|---|
| 3,800,552 A | 4/1974 | Sollami | |
| 4,278,090 A | 7/1981 | Van Gerven | |
| 4,381,652 A * | 5/1983 | Kunimoto | 62/46.1 |
| 4,946,460 A * | 8/1990 | Merry et al. | 606/24 |
| 5,078,713 A * | 1/1992 | Varney | 606/23 |
| 5,108,390 A * | 4/1992 | Potocky et al. | 606/21 |
| 5,800,487 A | 9/1998 | Mikus | |
| 5,800,488 A * | 9/1998 | Crockett | 607/105 |
| 5,910,104 A | 6/1999 | Dobak | |
| 5,978,697 A | 11/1999 | Maytal | |
| 5,993,444 A * | 11/1999 | Ammar et al. | 606/21 |
| 6,074,412 A * | 6/2000 | Mikus et al. | 607/105 |
| 6,251,105 B1 * | 6/2001 | Mikus et al. | 606/22 |
| 6,306,129 B1 * | 10/2001 | Little et al. | 606/23 |
| 6,551,309 B1 | 4/2003 | LePivert | |
| 6,767,346 B2 * | 7/2004 | Damasco et al. | 606/21 |
| 7,101,367 B2 * | 9/2006 | Xiao et al. | 606/21 |
| 2002/0022832 A1 | 2/2002 | Mikus | |
| 2003/0055415 A1 | 3/2003 | Yu | |

* cited by examiner

*Primary Examiner*—Ahmed M Farah
(74) *Attorney, Agent, or Firm*—Lawrence N. Ginsberg

(57) ABSTRACT

The threaded cryostat for a cryosurgical probe system includes an outer tube and a hollow elongated threaded element positioned within the outer tube. The threaded element has integral, external threads that extend from on an outer surface thereof. During operation a working fluid is transported in a first direction between a fluid supply line and a distal end of a cryosurgical probe within a first space defined within the threaded element. Working fluid is transported in a second direction between the distal end of the cryosurgical probe and the fluid supply line within a second space defined between the outer tube and the threaded element.

13 Claims, 3 Drawing Sheets

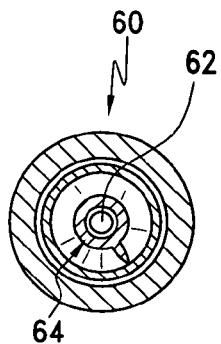 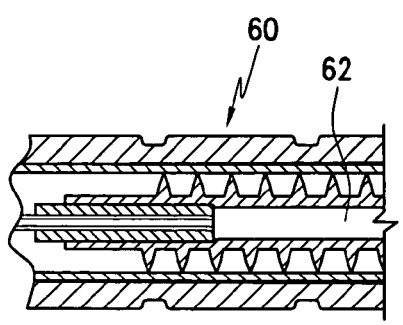 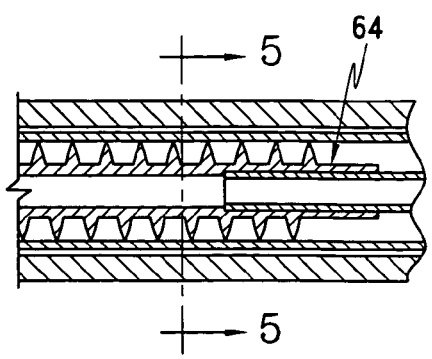
FIG. 5  FIG. 4
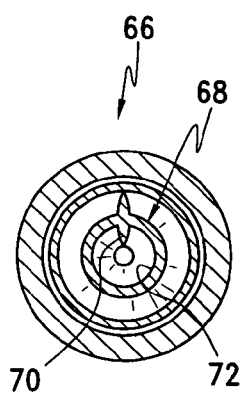 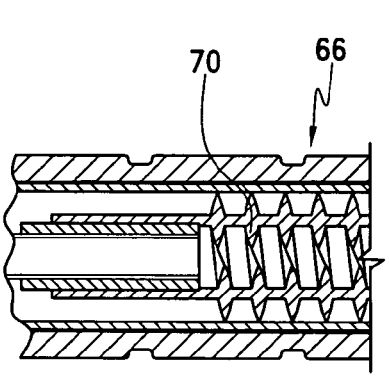 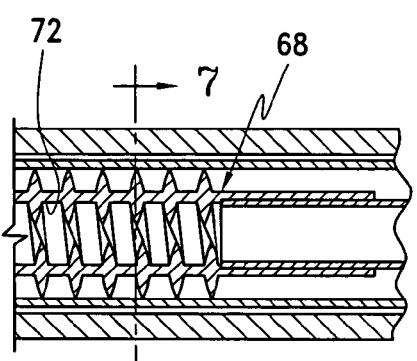
FIG. 7  FIG. 6
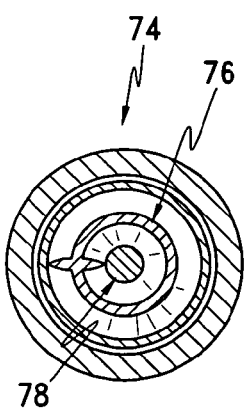 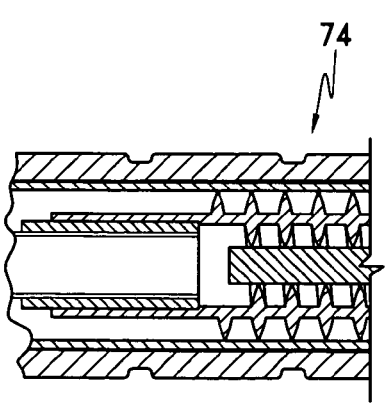 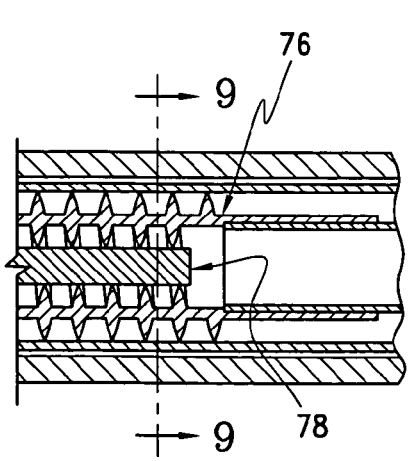
FIG. 9  FIG. 8

THREADED CRYOSTAT FOR CRYOSURGICAL PROBE SYSTEM

CROSS REFERENCE TO RELATED APPLICATIONS

This is a continuation-in-part of U.S. Ser. No. 10/828,031, entitled Detachable Cryosurgical Probe, filed Apr. 20, 2004 now U.S. Pat. No. 7,160,291, which is a continuation-in-part of U.S. Ser. No. 10/603,883, entitled Detachable Cryosurgical Probe, filed Jun. 25, 2003 now U.S. Pat. No. 7,207,985.

BACKGROUND OF THE INVENTION

1. Field of the Invention

The present invention relates to heat exchangers and more particularly to a threaded cryostat for use with cryosurgical probe systems.

2. Description of the Related Art

Cryosurgical probe systems presently being manufactured by present assignee, Endocare, Inc., use high pressure gas that is introduced to a cryostat that utilizes a finned tube helical coil heat exchanger for pre-cooling the high pressure gas prior to its introduction through a Joule-Thompson nozzle. This type of heat exchanger is disclosed in, for example, U.S. Pat. No. 6,074,412, entitled "Cryoprobe," issued to Mikus et al. Pre-cooling the incoming gas allows the cryosurgical probe to obtain lower temperatures.

U.S. Pat. No. 3,800,552, entitled "Cryogenic Surgical Instrument," issued to Sollami et al also discloses fin-tube heat exchanger in a cryosurgical probe system. The fins disclosed are individually attached fins such as discs or plates, or a continuous helically wound fin secured to the tube.

Generally, the prior art designs for these cryostats that have attached fins are relatively expensive to implement due to the somewhat complex manufacturing requirements. Furthermore, the bonding interface between the fins and the tube to which they are bonded provides a somewhat interrupted thermally conductive path.

What is desired is a cryosurgical probe in which the cryostat is relatively simple to manufacture yet still provides the heat exchange efficiency desired for proper operation.

SUMMARY OF THE INVENTION

In a broad aspect, the present invention is a threaded cryostat for a cryosurgical probe system that includes an outer tube; and, a hollow elongated threaded element positioned within the outer tube. The threaded element has integral, external threads that extend from on an outer surface thereof. During operation a working fluid is transported in a first direction between a fluid supply line and a distal end of a cryosurgical probe within a first space defined within the threaded element. Working fluid is transported in a second direction between the distal end of the cryosurgical probe and the fluid supply line within a second space defined between the outer tube and the threaded element. Utilizing a threaded cryostat over prior art designs that have attached fins is beneficial because the machined part provides cost benefits relative to the previous practice of attaching fins.

BRIEF DESCRIPTION OF THE DRAWINGS

FIG. 4 is an enlarged detailed cross-sectional view of another embodiment of a cryosurgical probe in which the cryostat portion does not contain a stranded wire bundle.

FIG. 5 is a cross-sectional view taken along line 5-5 of FIG. 4.

FIG. 6 is an enlarged detailed cross-sectional view of another embodiment of a cryosurgical probe in which the threaded element includes internal threads.

FIG. 7 is a cross-sectional view taken along line 7-7 of FIG. 6.

FIG. 8 is an enlarged detailed cross-sectional view of another embodiment of a cryosurgical probe in which the cryostat portion includes an inner tube with closed ends.

FIG. 9 is a cross-sectional view taken along line 9-9 of FIG. 8.

DETAILED DESCRIPTION OF THE INVENTION

Figure 1:
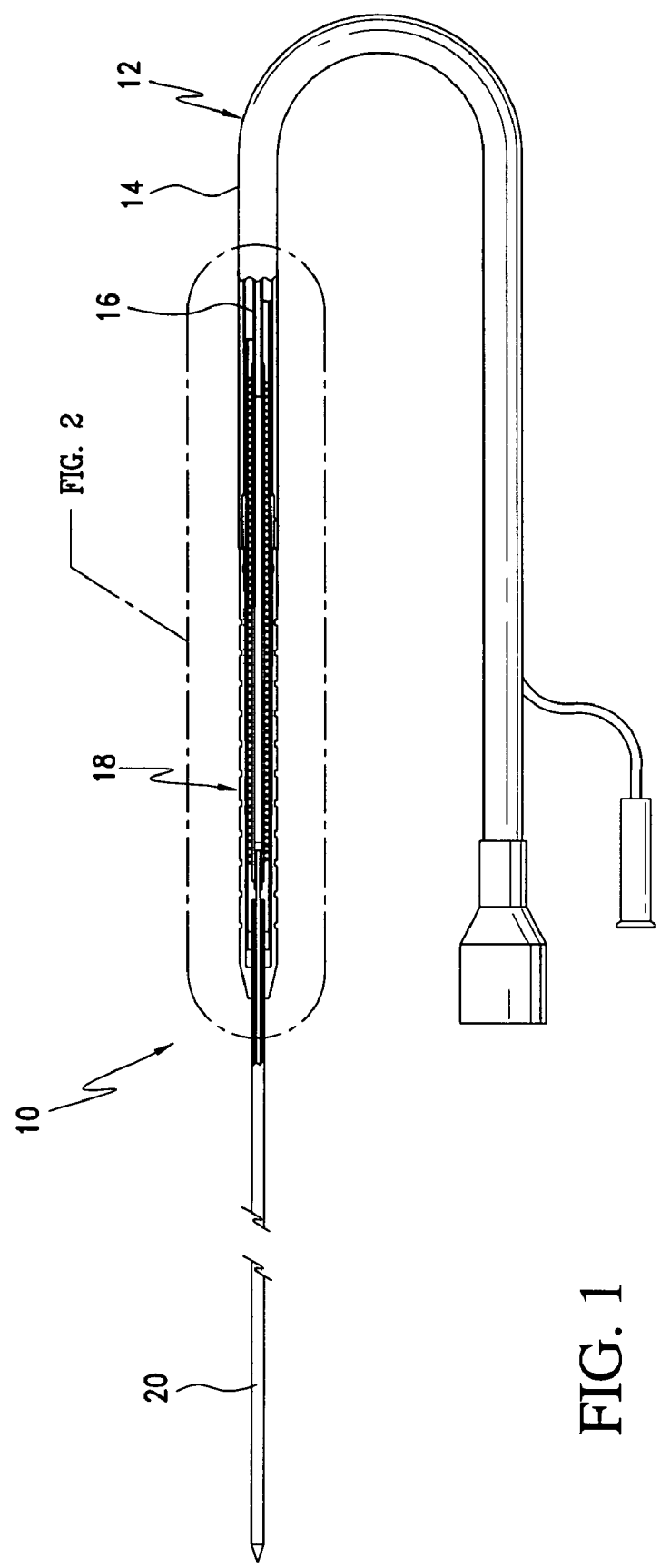
FIG. 1 is a side elevational view, in partial cross-section, of a cryosurgical probe system of the present invention.
Figures 2, 3:
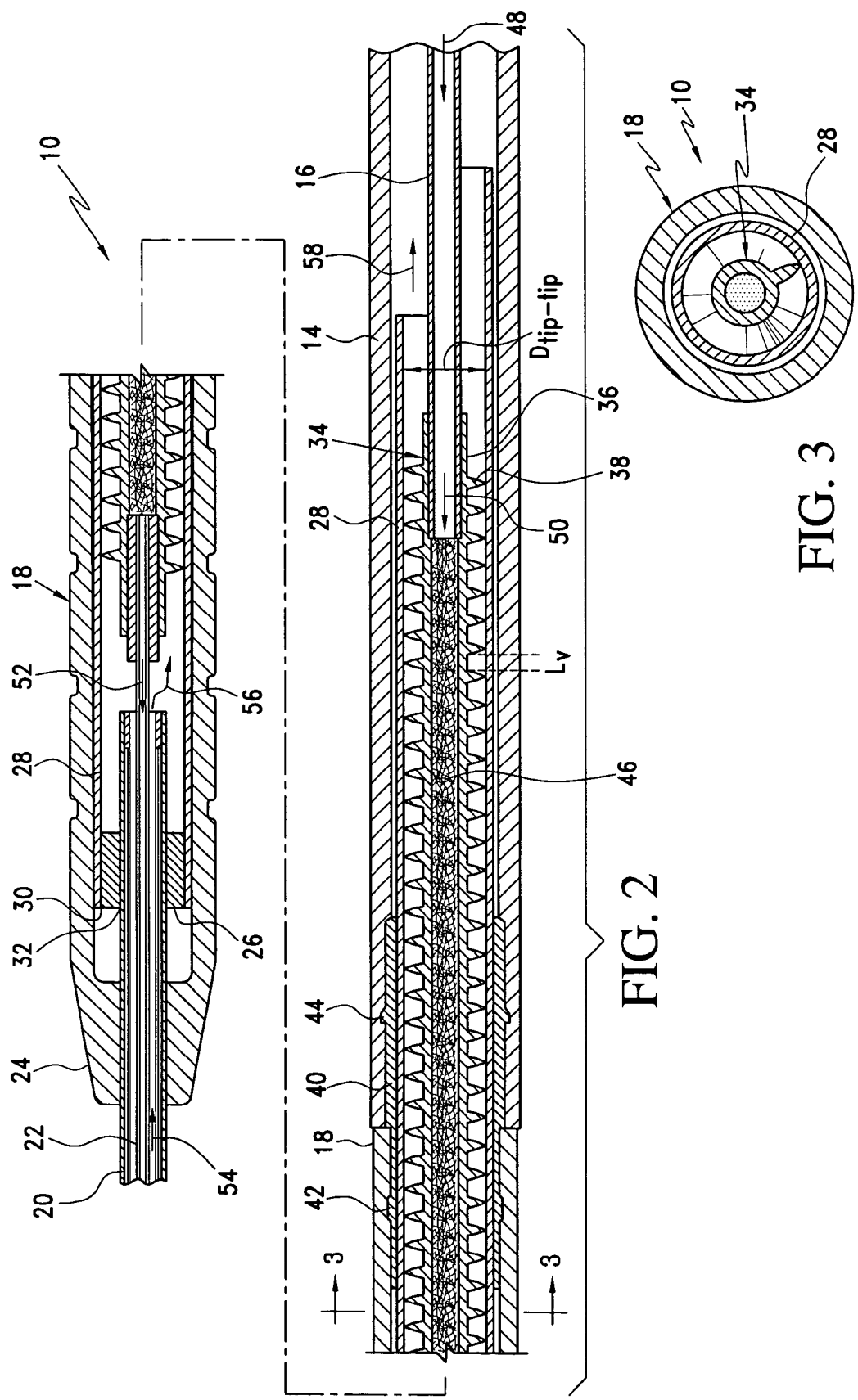
FIG. 2 is an enlarged detailed cross-sectional view of the cryostat portion of the cryosurgical probe, taken from FIG. 1.
FIG. 3 is a cross-sectional view taken along line 3-3 of FIG. 2.

Referring now to the drawings and the characters of reference marked thereon, FIGS. 1 and 2 illustrate a preferred embodiment of the cryosurgical probe system of the present invention, designated generally as 10. The cryosurgical probe system 10 includes a fluid supply line, designated generally as 12, that is connected at an inlet section 14 to a source (not shown) of cryogenic fluid. The fluid source may be, for example, a cryosurgical system such as that manufactured by present assignee, Endocare, Inc., Irvine, Calif. Such a cryosurgical system typically utilizes argon gas from an argon gas source 18 to provide Joule-Thomson cooling of the cryosurgical probes. Alternatively, nitrogen can be used. Alternatively, a fluid supply system can be utilized that does not require an external fluid supply source. Heating of the cryosurgical probes is typically provided by a helium gas source for providing a helium gas flow through the Joule-Thomson nozzle of the cryosurgical probe. This provides a heating effect. Such heating of the cryosurgical probes is provided to unstick the probes from the treated tissue for cryoprobe removal. Alternatively, other methods for warming may be used such as electrical heating via heated coils, microwave or RF heating.

The fluid supply line 12 preferably includes a flexible hose, i.e. working fluid outlet section 14, for containing a return gas flow. The hose 14 may be formed of any suitable material such as flexible PVC. Contained within the flexible hose 14 is a high pressure gas feed line 16, i.e. high pressure working fluid inlet section.

The cryosurgical probe assembly 10 includes a cryosurgical probe housing assembly or handle assembly 18. The housing assembly 18 supports a cryosurgical probe sheath 20. The sheath 20 contains a Joule-Thomson extension tube 22 that terminates with a Joule-Thomson nozzle. The cryosurgical probe sheath 20 is supported at a distal section 24 of the handle assembly 18. It is also supported via a safety washer 26 and terminal end of an extension shaft 28 at a more intermediate section of the handle. Solder joints 30, 32 provide the required securing of the washer 26 to the extension shaft 28 and sheath 20. The cryosurgical sheath 20 defines a freezing zone for providing target tissue ablation.

The threaded cryostat of the present invention, designated generally as 34, includes the extension shaft 28 that serves as the outer tube of the cryostat 34. A hollow elongated threaded element 36 is positioned within the outer tube 28. The threaded element 36 has integral, external threads 38 that extend from an outer surface thereof. These threads 38 function as fins for the conduction of heat. The threaded element 36 is preferably formed of copper alloy although other suitable material may be used, such as silver, aluminum, beryllium, brass, gold, tin, etc. The threads are helical. In the present preferred embodiment the threads have a triangular cross-section with the apex of the triangle forming an angle of about 26 degrees. The length $L_v$ of each valley section may be, for example, about 0.036 inches. The tip-to-tip diameter, $D_{tip-tip}$, may be about 0.164 inches. The $D_{tip-tip}$ range may be in a range of about of about 0.060-0.75 inches, preferably in a range of about 0.10-0.25 inches. The threaded element 36 has a tight fit within the outer tube 28. A stepped anchor 40 with bumps 42 and 44 secure the handle 18 and hose 14.

An interior space within the threaded element 36 contains stranded wire material 46. The stranded wire material 46 may be formed of, for example, copper, tin or zinc—or combinations thereof.

In operation, working fluid is transported in from the high pressure working fluid inlet section 16 of the fluid supply line through the first space defined by a central opening in the threaded element 34, as indicated by arrows 48, 50. It passes through the stranded wire material 46 as shown by arrow 52. The high pressure working fluid is then directed through the Joule-Thomson extension tube 22 and through the Joule-Thomson nozzle. The discharge of the Joule-Thomson nozzle is directed through a space between the Joule-Thomson extension tube 22 and the sheath 20, as shown by arrow 54. It is then directed through the space defined between the outer tube 22 and the threaded element 34, i.e. through the threads 38, as shown by arrow 56. It then flows through the working fluid outlet section, as shown by arrow 58. The stranded wire bundle 46 of material maximizes the amount of thermal conductivity.

Referring now to FIGS. 4 and 5 another embodiment of the cryosurgical probe assembly is illustrated, designated generally as 60. This embodiment is very similar to the previous embodiment; however, the stranded wire bundle is omitted and the central opening 62 of the threaded element 64 is empty. This results in a decreased thermal efficiency; however, it has the benefit of reduced parts and manufacturing costs.

Referring now to FIGS. 6 and 7 another embodiment of the cryosurgical probe assembly is illustrated, designated generally as 66. This embodiment is very similar to the previous embodiment; however, in this embodiment the threaded element 68 includes internal threads 70 that extend from an inner surface 72 thereof. These internal threads 70 provide an increased surface area.

Referring now to FIGS. 8 and 9 another embodiment of the cryosurgical probe assembly is illustrated, designated generally as 74. This embodiment is very similar to the previous embodiment; however, in this embodiment the threaded element 76 includes an inner tube 78 with closed ends. (As in the previous embodiment this embodiment also includes internal threads 80 that extend from an inner surface of the threaded element 76.) The inner tube 78 directs the flow in a helical fashion around the threaded passageways.

Although the present invention has been discussed above with respect to a cryosurgical probe having with a rigid outer sheath, the cryosurgical probe may be made to be malleable by including at least one malleable segment thereon. Malleable segments are formed of material that permit reshaping and bending to reposition the ablating surface for greater ablation precision. An example of a cryosurgical probe having malleable characteristics is disclosed and claimed in co-pending patent application Ser. No. 09/957,337, Pub. No. US 2003/0055415 A1, filed on Sep. 20, 2001 entitled Malleable Cryosurgical Probe, incorporated in its entirety herein by reference.

One method for providing malleable characteristics includes providing a malleable shaft with a bellows portion. Patent application Ser. No. 10/057,033, Pub. No. US 2003/0055416 A1, filed on Jan. 23, 2002, and issued as U.S. Pat. No. 6,767,346, entitled Cryosurgical Probe With Bellows Shaft, incorporated in its entirety herein by reference, discloses use of a bellows portion for providing the necessary reshaping and bending.

Thus, while the preferred embodiments of the devices and methods have been described in reference to the environment in which they were developed, they are merely illustrative of the principles of the invention.

For example, multiple Joule Thomson ports may be utilized and made to be axially spaced. This provides the ability to create an elongated iceball.

Other embodiments and configurations may be devised without departing from the spirit of the invention and the scope of the appended claims.

The invention claimed is:

1. A threaded cryostat for a cryosurgical probe system, comprising:
   a) an outer tube; and,
   b) a hollow elongated threaded element positioned within said outer tube, said threaded element having integral, external threads that extend from on an outer surface thereof,
   wherein during operation a working fluid is transported in a first direction between a fluid supply line and a distal end of a cryosurgical probe within a first space defined within said threaded element; and, working fluid is transported in a second direction between the distal end of the cryosurgical probe and the fluid supply line within a second space defined between said outer tube and said threaded element.

2. The threaded cryostat of claim 1 wherein the tip-to-tip diameter of said external threads of said threaded element are in a range of about 0.060-0.75 inches.

3. The threaded cryostat of claim 2 wherein said threaded element is formed of a copper alloy.

4. The threaded cryostat of claim 1 wherein the tip-to-tip diameter of said external threads of said threaded element are in a range of about 0.10-0.25 inches.

5. The threaded cryostat of claim 1 wherein stranded wire material is positioned within said threaded element for enhanced heat exchange.

6. The threaded cryostat of claim 1 wherein said threaded element includes internal threads that extend from an inner surface thereof.

7. The threaded cryostat of claim 1 wherein said threaded element includes internal threads that extend from an inner surface thereof and wherein said cryostat further comprises an inner tube positioned within said threaded element, said inner tube being closed at both ends.

8. A cryosurgical probe assembly, comprising:
   a) a cryosurgical probe housing assembly;
   b) a fluid supply line including a high pressure working fluid inlet section and working fluid outlet section, said fluid supply line being connected to said cryosurgical probe housing assembly;

c) a cryosurgical probe sheath supported by said cryosurgical probe housing assembly, said sheath containing a Joule-Thomson nozzle for the discharge of high pressure working fluid, said cryosurgical probe sheath defining a freezing zone for providing target tissue ablation; and, d) a threaded cryostat supported by said cryosurgical probe housing assembly, said threaded cryostat, comprising:

i. an outer tube; and;

ii. a hollow elongated threaded element positioned within said outer tube, said threaded element having integral, external threads that extend from an outer surface thereof, wherein during operation working fluid is transported in a first direction between the fluid supply line and a distal end of a cryosurgical probe within a first space defined within said threaded element; and, working fluid is transported in a second direction between the distal end of the cryosurgical probe and the fluid supply line within a second space defined between said outer tube and said threaded element.

9. The cryosurgical probe assembly of claim 8 wherein:

said first direction is from said high pressure working fluid inlet section of said fluid supply line through said first space defined by a central opening in said threaded element, said high pressure working fluid then being directed through a Joule-Thomson extension tube and through said Joule-Thomson nozzle; and, said second direction is from the discharge of the Joule-Thomson nozzle, through said second space defined between said outer tube and said threaded element and then through said working fluid outlet section of said fluid supply line.

10. The cryosurgical probe assembly of claim 8 wherein said threads are helical.

11. The cryosurgical probe assembly of claim 8 wherein stranded wire material is positioned within said threaded element for enhanced heat exchange.

12. The cryosurgical probe assembly of claim 8 wherein said threaded element includes internal threads that extend from an inner surface thereof.

13. The cryosurgical probe assembly of claim 9 wherein said threaded element includes internal threads that extend from an inner surface thereof and wherein said cryostat further comprises an inner tube positioned within said threaded element, said inner tube being closed at both ends.

* * * * *